(12) United States Patent
Wang et al.

(10) Patent No.: US 11,318,288 B2
(45) Date of Patent: May 3, 2022

(54) INSTRUMENT FOR DELIVERING SUBSTANCES INTO THE ANATOMY

(71) Applicant: GYRUS ACMI, INC., Southborough, MA (US)

(72) Inventors: Huisun Wang, Maple Grove, MN (US); Kester J. Batchelor, Mound, MN (US)

(73) Assignee: Gyrus ACMI, Inc., Westborough, MA (US)

(*) Notice: Subject to any disclaimer, the term of this patent is extended or adjusted under 35 U.S.C. 154(b) by 0 days.

(21) Appl. No.: 15/936,791

(22) Filed: Mar. 27, 2018

(65) Prior Publication Data

US 2019/0298975 A1 Oct. 3, 2019

(51) Int. Cl.
*A61M 25/00* (2006.01)
*A61M 25/10* (2013.01)
(Continued)

(52) U.S. Cl.
CPC ......... *A61M 25/10* (2013.01); *A61B 10/0233* (2013.01); *A61B 10/0266* (2013.01); *A61M 25/0074* (2013.01); *A61B 1/00082* (2013.01); *A61B 1/2676* (2013.01); *A61B 17/3401* (2013.01); *A61B 17/3403* (2013.01);
(Continued)

(58) Field of Classification Search
CPC .............. A61M 25/10; A61M 25/0074; A61M 25/0067; A61M 5/322; A61M 2025/0079; A61M 2025/09008; A61M 2025/0905; A61M 2025/1013; A61M 2025/105; A61M 2025/1086; A61M 2025/1093; A61M 2025/0024; A61M 2025/007; A61M 2025/1081; A61B 17/3401; A61B 17/3403; A61B 17/3415; A61B 17/3417; A61B 17/221; A61B 1/00082; A61B 1/00085; A61B 2017/3409; A61B 2017/32113;
(Continued)

(56) References Cited

U.S. PATENT DOCUMENTS

| 6,544,223 | B1 | 4/2003 | Kokish |
| 7,066,904 | B2 | 6/2006 | Rosenthal et al. |
| 7,115,299 | B2 | 10/2006 | Kokish |
| 9,216,271 | B2 * | 12/2015 | Cox .................. A61M 25/1002 |

(Continued)

FOREIGN PATENT DOCUMENTS

WO 2012/030587 A1 3/2012

OTHER PUBLICATIONS

Extended European Search Report for European Application No. 19162882.5; dated Jun. 13, 2019.

*Primary Examiner* — Nathan R Price
*Assistant Examiner* — Tania Ismail
(74) *Attorney, Agent, or Firm* — Clements Bernard Baratta Walker (57) ABSTRACT

A medical instrument that includes a needle and an expandable member located at a distal end of the needle. The expandable member includes a blocking member. The expandable member is configured to move tissue away from a distal end of the needle and/or from a distal end of a tubular member that is in fluid communication with a substance source. A substance is configured to be expelled into the anatomy through the expandable member. The blocking member is configured to restrict or prevent the substance from being expelled through the portion of the expandable member that includes the blocking member.

3 Claims, 5 Drawing Sheets

(51) Int. Cl.
    *A61B 10/02*     (2006.01)
    *A61B 1/267*     (2006.01)
    *A61B 10/04*     (2006.01)
    *A61B 17/34*     (2006.01)
    *A61M 5/32*     (2006.01)
    *A61M 25/09*     (2006.01)
    *A61B 1/00*     (2006.01)

(52) U.S. Cl.
    CPC ....... *A61B 17/3415* (2013.01); *A61B 17/3417* (2013.01); *A61B 2010/045* (2013.01); *A61M 5/322* (2013.01); *A61M 25/0067* (2013.01); *A61M 2025/0079* (2013.01); *A61M 2025/09008* (2013.01); *A61M 2025/105* (2013.01)

(58) Field of Classification Search
    CPC ........ A61B 2017/22084; A61B 1/2676; A61B 2010/045
    See application file for complete search history.

(56) References Cited

U.S. PATENT DOCUMENTS

| | | |
|---|---|---|
| 2004/0044308 A1 | 3/2004 | Naimark et al. |
| 2005/0131269 A1* | 6/2005 | Talmadge ............ A61B 10/025 600/3 |
| 2007/0071789 A1 | 3/2007 | Pantelidis et al. |
| 2007/0142770 A1 | 6/2007 | Rioux et al. |
| 2008/0009875 A1 | 1/2008 | Sankaran et al. |
| 2009/0105642 A1* | 4/2009 | Leonard ............ A61M 25/1011 604/103.09 |
| 2010/0114087 A1 | 5/2010 | Edwards et al. |
| 2011/0054383 A1 | 3/2011 | Boezaart |
| 2014/0046252 A1* | 2/2014 | Boatman ............ A61M 25/1011 604/101.02 |
| 2014/0276051 A1 | 9/2014 | Hoffman |
| 2015/0320910 A1 | 11/2015 | Klein et al. |
| 2016/0074635 A1* | 3/2016 | Consigny ................ A61B 17/22 604/103.02 |
| 2017/0079679 A1* | 3/2017 | Pigott ............ A61B 17/320725 |
| 2017/0196717 A1 | 7/2017 | Fulkerson et al. |
| 2017/0290605 A1 | 10/2017 | Bakri |
| 2018/0078243 A1 | 3/2018 | Rocha-Singh et al. |

\* cited by examiner

INSTRUMENT FOR DELIVERING SUBSTANCES INTO THE ANATOMY

FIELD

These teachings relate to an instrument for delivering substances into the anatomy.

BACKGROUND

Needles are used in a variety of medical procedures for delivering substances into the anatomy. Accurately delivering substances to a site of interest in the anatomy is a challenge some technicians face during a medical procedure.

For example, an end of the needle may be blocked or obstructed with tissue or objects inside the anatomy, which may undesirably block, deflect, or otherwise obstruct delivery of the substance to the anatomy. For example, some needles may unintentionally deliver or expel substances toward tissue in the anatomy that is not intended to be treated with the substance, which may cause damage to otherwise healthy tissue. Some needles may be configured to deliver or expel a substance into the anatomy, which may then unintentionally leak back towards a distal end of the needle and/or away from the intended area to be treated, which may undesirably prolong a medical procedure, and/or require the technician to reposition the needle inside the anatomy, which may cause trauma to tissue inside the anatomy.

It may therefore be desirable to have a medical instrument that overcomes at least some of the aforementioned difficulties.

SUMMARY

These teachings provide a medical instrument comprising a needle and an expandable member extending distally beyond a distal end of the needle. The expandable member is configured or enabled to move or deflect tissue away from a distal end of a tubular member that is in fluid communication with a fluid source. The substance is then delivered or expelled into the expanded anatomy through the expandable member.

To provide for the substance to only be delivered to desired areas inside the anatomy, the medical instrument includes a blocking member that is enabled or configured to block the substance from being expelled through certain areas of the expandable member that includes the blocking member, for example through or from a proximal portion of the expandable member. This functions to advantageously provide for delivery of substances only toward tissue in the anatomy that is intended to be treated with the substance (i.e., tissue that is located at or near a central and distal portion of the expandable member), while preventing delivery of the substance to tissue in the anatomy that is not intended to be treated with the substance (i.e., tissue that is located at or near a proximal portion of the expandable member. This allows a technician greater control of where the substance is being delivered in the anatomy. Moreover, by delivering or expelling the substance only from a center and/or distal portion of the expandable member, chances of the substance leaking back towards the distal end of the tubular member and/or needle is reduced or prevented. This reduces chances of the substance flowing back into the needle and/or tubular member or even out of the anatomy through a puncture point where the needle penetrates the anatomy.

These teachings provide a medical instrument comprising: a needle; a tubular member located inside of the needle; an expandable member enabled to extend from a distal end of the tubular member; and a blocking member disposed around a proximal portion of the expandable member. The expandable member is enabled or configured to expand and collapse. The expandable member comprises a plurality of fingers that are connected to a distal end of the tubular member and enabled or configured to expand and collapse. The blocking member is flexible and enabled or configured to expand and collapse with the fingers as the fingers expand and collapse. The expandable member is configured to expand to move tissue away from a distal end of the tubular member, a distal end of the needle, or both. The medical instrument is configured to deliver a substance to the anatomy through the expandable member. The blocking member is configured to block and prevent the substance from being expelled into the anatomy through the proximal portion of the expandable member.

These teachings provide a method, comprising inserting the needle of the medical instrument according to any of these teachings into an anatomy. The method includes expanding the expandable member to move tissue away from the distal end of the needle and/or tubular member. The method includes expelling a substance into the anatomy through the expandable member. The medical device comprises a blocking member that is configured to block the substance from being expelled into the anatomy through or from a portion of the expandable member that includes the blocking member.

These teachings provide a method comprising inserting the needle of the medical instrument according to any of these teachings into the anatomy. The method includes moving the tubular member in a distal direction so that the expandable member is moved distally beyond the distal end of the needle so that the fingers of the expandable member expand and move tissue away from the distal end of the tubular member. The method includes expelling a substance into the anatomy through the expandable member. The medical device includes a blocking member that is configured to block the substance from being expelled into the anatomy from the portion of the expandable member that includes the blocking member.

DETAILED DESCRIPTION

These teachings provide a medical device. The medical device may be used in any suitable medical procedure or non-medically related procedure. The medical device can be used to treat a lung. For example, the medical device can be used to evenly and consistently deliver, distribute, and/or provide a therapeutic substance into the lung for lung cancer therapy. The medical device may comprise a bronchoscope, a viewing device, a medical instrument, such as a needle, a tubular member, an expandable member, a blocking member, a substance source, or a combination thereof.

The medical device may comprise a bronchoscope. The bronchoscope may be used to withdrawal foreign bodies, tissue samples, blood, or a combination thereof from the anatomy; may be used to visually inspect a site of interest in the anatomy, or both. The bronchoscope may be used for examining, treating, and/or diagnosing lung growth, lung problems, lung cancer, lymph node(s), atelectasis, suspected interstitial lung disease, a lung rejection after a lung transplant, and/or to remove fluid or mucus plugs from the airways of a patient. The bronchoscope may provide for the insertion, manipulation, and/or operation of any medical instrument in the anatomy; delivery of one or substances into the anatomy, or both.

The medical device may comprise a viewing device. The viewing device may be used to view or observe an internal portion of the anatomy, view the medical instrument inside the anatomy at a site of interest, or both. The viewing device may provide a technician or surgeon with the ability to observe at least a portion of the needle inside the anatomy; help indicate a depth of penetration of the needle into a site of interest in the anatomy; assist in orienting the needle or expandable member relative to a site of interest in the anatomy; view tissue being expanded inside the anatomy with the expandable member; or a combination thereof. The viewing device may be any device configured to receive echo signals reflected and/or deflected from any markings, scribes, echogenic features, etc. disposed on the needle, the tubular member, the expandable member, the blocking member, or a combination thereof. Exemplary viewing devices may include one or more ultrasounds, radiographic instruments, fluoroscopic visualizations, X-rays, transducers, transmitters, etc.

One or more medical instruments may be used with the medical device. Alternatively, the medical instrument may be used without the medical device disclosed herein. For example, the medical instrument comprises a needle, a tubular member, an expandable member, and a blocking member. The needle, tubular member, expandable member, and blocking member may be used as a stand-alone instrument, without the bronchoscope, viewing device, or both. The medical, instrument includes a sheath. However, the needle, tubular member, expandable member, and blocking member may be used as a stand-alone instrument without a sheath (i.e., an outer surface of the length of the needle may be exposed and not covered by a sheath).

The medical instrument may include a needle. The needle may function to pierce or puncture the anatomy. The needle may function to provide a passageway or conduit for the tubular member, the expandable member, the blocking member, or a combination thereof to be inserted into the anatomy and then steered to a site of interest inside the anatomy. The needle may function to provide a passageway for the delivery of one or more substances from the substance source to the site of interest in the anatomy. The needle may be a coring needle, a sampling needle, a transbronchial aspiration needle, a puncturing needle, a guiding needle, the like, or a combination thereof.

The needle may be at least partially resilient, expandable, collapsible, formable, deformable, or a combination thereof. The needle may at least partially flexible, bendable, articulable, or a combination thereof to allow for the needle to flex, bend, and/or articulate while the needle is inserted into the anatomy and steered to the site of interest.

The needle may have any length suitable for use in any medical procedure. The needle may have any size or gauge suitable for use in any medical procedure. For example, the needle may be about 25 gauge or more, about 22 gauge, about 21 gauge, or about 19 gauge or less, etc. The needle may have any cross section that is suitable for use in any medical procedure. For example, the cross section of the needle may be generally circular, oval, square, or any other suitable shape.

The needle may be generally hollow to provide for the tubular member and the expandable member to be located inside the needle and moveable inside the needle. The tubular member and/or expandable member may be moved along a longitudinal length of the needle and/or may be rotated within the needle about a longitudinal axis of the needle.

The needle may be moved within the sheath. Relative to the sheath or the anatomy, the needle may be moved axially, proximally, distally, rotationally, or a combination thereof. Distally moving the needle may function to expose a distal end or tip of the needle from within the sheath, while proximally moving the needle may function to hide, secure, or protect the distal end or tip of the needle inside the sheath.

The medical instrument may comprise a sheath. The sheath may function to cover or protect at least a portion of the needle. The sheath may function provide an area to grip or handle the medical instrument, without directly contacting the needle, the distal end or tip of the needle, or both. The sheath may function to protect or cover a distal end tip of the needle when the needle is retracted inside the sheath. The sheath may or may not be inserted into the anatomy or site of interest during a medical procedure.

The sheath may be at least partially resilient, expandable, collapsible, formable, deformable, or a combination thereof. The sheath may at least partially flexible, bendable, articulable, or a combination thereof to allow for the needle to flex, bend, and/or articulate while the needle is inserted into the anatomy and steered to the site of interest.

The needle may be axially moved or extended in a distal direction relative to the sheath so that the distal end or tip of the needle can project out of a distal end of the sheath. The needle may be axially moved or retracted in a proximal direction relative to the sheath so that the distal end or tip of the needle can be encircled by the sheath and thereby protected by the sheath. The needle may be rotated about or around a longitudinal axis of the needle, sheath, or both. The needle may be axially and/or rotationally moved relative to the sheath by manipulating one or more of the user controls located on the medical device, the medical instrument, at a remote location, or a combination thereof. For example, needle may be axially and/or rotationally moved relative to the sheath by moving, depressing, or otherwise manipulating one or more buttons, levers, triggers, knobs, foot pedals, or a combination thereof.

The medical instrument may comprise a tubular member. The tubular member may function to provide a passageway between one or more substance sources and the expandable member to allow or provide for the one or more substances to be delivered, flow, or pass therebetween.

A proximal end of the tubular member may be in fluid communication with a substance source, or one or more tubes or passageway that are in fluid communication with the substance source. A distal end of the tubular member may be connected to the expandable member, the blocking member, or both.

The tubular member may be at least partially resilient, expandable, collapsible, formable, deformable, or a combination thereof. The tubular member may at least partially flexible, bendable, articulable, or a combination thereof to allow for the tubular member to flex, bend, and/or articulate while the needle is inserted into the anatomy and steered to the site of interest.

The tubular member may be moved within the needle. Relative to the needle, sheath, and/or the anatomy, the tubular member may be moved axially, proximally, distally, rotationally, or a combination thereof. Distally moving the tubular member so that the expandable member is moved beyond a distal end or distal tip of the needle may function to expose the expandable member from within the needle and/or allow the expandable member to move into the expanded configuration. Proximally moving the tubular member so that the expandable member is moved proximally into or beyond or within the distal end or distal tip of the needle may function to hide the expandable member and/or provide for the expandable member to move into the collapsed configuration. The tubular member may be moved by manipulating one or more of the user controls located on the medical device, the medical instrument, at a remote location, or a combination thereof. For example, the tubular member may be moved by moving, depressing, or otherwise manipulating one or more buttons, levers, triggers, knobs, foot pedals, or a combination thereof. The tubular member may be moved by pushing, pulling, or rotating a pull wire in communication with the tubular member to corresponding push, pull, or rotate the tubular member and the expandable member located at a distal end of the tubular member.

The medical instrument comprises an expandable member. The expandable member may be opened or expanded to move or push tissue, objects, or other features away from the distal end of the needle and/or the distal end of the tubular member. The expandable member may be opened or expanded to move or push tissue, objects, or other features inside the anatomy away from the distal end of the needle and/or the distal end of the tubular member so that one or more substances can be expelled or delivered from the tubular member without the tissue, objects, or other features inside the anatomy contacting, blocking, deflecting, interfering with, or otherwise obstructing delivery or flow of the substance.

The expandable member may be opened or expanded to move or push tissue, objects, or other features inside the anatomy away from the distal end of the needle and/or a distal end of the tubular member to clear or open a path for the needle and/or tubular member so that the needle and/or tubular member can be steered to a site of interest inside the anatomy without obstruction. The expandable member may be opened or expanded to move or push tissue, objects, or other features inside the anatomy away from the distal end of the needle and/or a distal end of the tubular member so that a location or position of the distal end of the needle and/or tubular member can be viewed with the viewing member of the medical device without obstruction.

Without such an expanding member, tissue and/or objects inside the anatomy may be located near or in contact with the needle or tubular member, which may undesirably block or deflect the substance from being delivered to the tissue or anatomy. This may undesirably require the technician to repeatably insert and remove the needle, manipulate and/or reposition the needle inside the anatomy, or a combination thereof in order to deliver the substance to the anatomy, which may prolong a medical procedure, contribute to an increase in wasted substance, contribute to patient trauma, and/or contribute to technician frustration. Moreover, tissue or objects inside the anatomy that block the distal end of the needle and/or tubular member may inhibit or make steering the needle and/or tubular member to a site of interest difficult or cumbersome. Furthermore, tissue or objects inside the anatomy that block the distal end of the needle and/or tubular member may inhibit or make it difficult to view the distal end of the needle and/or tubular member with the viewing device.

The expandable member may be moved between an open or expanded configuration and a closed or collapsed configuration. The expandable member may be configured to be moved; may be enabled to be moved; may be provided to be moved, etc. between an open or expanded configuration and a closed or collapsed configuration. The closed or collapsed configuration may be referred to as a first state, which is when or at times when the expandable member is not extended or moved beyond a distal end of the needle. The open or expanded configuration may be referred to as a second state, which is when the or at times when at least a portion of the expandable member is extended beyond the distal end of the needle.

The expandable member is moved or deployed into the open or expanded configuration by moving the expandable member, the tubular member, or both so that a force or object is no longer in contact or acting on the expandable member. The expandable member is moved or deployed into the open or expanded configuration by moving the expandable member, the tubular member, or both in a distal direction and distally beyond a distal end of the needle so that the needle is no longer in contact with or applies a lower force on the expandable member. In the open or expanded configuration, the expandable member is at least partially located outside or distal of the distal end of the needle.

The expandable member is moved in to the closed or collapsed configuration by moving the expandable member, the tubular member, or both so that a force or object contacts or applies a force on the expandable member. The expandable member is moved into the closed or collapsed configuration by moving or drawing the expandable member, the tubular member, or both in a proximal direction into the needle, proximally beyond a distal end of the needle so that the needle contacts or applies a force on the expandable member. In the closed or collapsed configuration, the expandable member is at least partially located inside the needle.

In the open or expanded configuration, the expandable member may have a spherical or cylindrical cross section. A cross section of the expandable member in the open or expanded configuration is greater or larger than a cross section of the expandable member in the closed or collapsed configuration.

The expandable member may be a balloon. The expandable member may be a basket or cage that can also be used for capturing and removing objects from within the anatomy.

The expandable member may comprise one or more fingers. The one or more fingers may function or be made or configured to expand and collapse between an open or expanded configuration, and a closed or collapsed configuration, respectively. The plurality of fingers may be enabled or configured to expand after at least a portion of the expandable member is moved distally beyond the distal end of the needle. The plurality of fingers may be enabled or configured to collapse after at least a portion of the expandable member is moved proximally into the needle or proximally within a distal end of the needle.

The fingers or wires may be made of a metal. For example, the fingers or wires may be made of a memory or shape memory alloy, nickel-titanium based alloys like Nitinol, stainless steel, and/or a chromium cobalt alloy. The fingers or wires may be made of a shape memory plastic, such as a thermoplastic plastic or polyurethane. The memory or shape metal may function to allow the fingers and/or the expandable member to expand into the open or expanded configuration after the expandable member and/or fingers are moved distally beyond the needle so that the needle no longer applies a force thereon. The memory or shape metal may function to allow the fingers and/or the expandable member to collapse into the closed or collapsed configuration after the expandable member and/or fingers are moved proximally inside the needle so that the needle applies a force thereon and forces or moves or deflects the fingers or wires into the closed or collapsed configuration.

The fingers may be oriented in a helical manor between a proximal and distal end of the expandable member. The fingers may be interconnected or cross over and under one another between a proximal and distal end of the expandable member. The fingers may be wound or weaved together between a proximal and distal end of the expandable member. The fingers may be connected to one another via mechanical fasteners between a proximal and distal end of the expandable member. The fingers may be generally straight between a proximal and distal end of the expandable member. Generally straight means that the individual fingers do not contact or cross over or under each other between a proximal and distal end of the expandable member.

The fingers may be attached to a distal end of the tubular member. The fingers may be attached to the tubular member so as to not inhibit or interfere with the substance passing, through or exiting from a distal end of the tubular member. The fingers may be attached at a wire collector at a distal end of the expandable member. The distal end of the expandable member or wire collector may be sufficiently rigid to maintain the fingers, but sufficiently flexible, elastic, bendable and/or deflectable to reduce patent discomfort when the tubular member and/or expandable member is moved or extended in a distal direction and the distal end or wire collector contacts tissue at the site of interest in the anatomy. For example, the distal end or wire collector may be formed of a rubber or urethane material. Alternatively, the expandable member may be free of a wire collector, and instead, the fingers may be weaved or connected together at a distal end and may optionally be connected together with a mechanical connector such as a weld or crimp.

One or more gaps or apertures may be defined between the one or more fingers or wires of the expandable member. The one or more gaps or apertures defined between the one or more fingers or wires of the expandable member function to provide an area where the substance can be delivered, directed, deflected, distributed, and/or expelled into the anatomy from the tubular member, the expandable member, or both.

The one or more gaps or apertures may run along an entire length of the expandable member, between a proximal and distal end thereof. The one or more gaps or apertures may run only along a portion of an entire length of the expandable member, between a proximal and distal end thereof. For example, the blocking member may block or cover a portion of the expandable member, while leaving one or more gaps or apertures defined between the fingers or wires of the expandable member exposed.

The medical instrument may comprise a blocking member. The blocking member may function to block, deflect, or prevent delivery of a substance from certain areas or portions of the medical instrument. For example, the blocking member may function to block, deflect, or prevent delivery of a substance from a proximal portion of the expandable member, a distal portion of the expandable member, a central portion of the expandable member that is defined between the distal and proximal portions of the expandable member, or a combination thereof.

The blocking member may function to block, deflect, or prevent delivery of a substance to certain areas or portions of the anatomy. That is, the blocking member may function to block, deflect, or prevent delivery of a substance to areas or portions of the anatomy that are located near the blocking member. For example, the blocking member may function to block, deflect, or prevent delivery of a substance to portions of the anatomy located near or adjacent a proximal portion of the expandable member, a distal portion of the expandable member, a central portion of the expandable member that is defined between the distal and proximal portions of the expandable member, or a combination thereof.

The blocking member may function to more evenly expel a substance from an entire area or portion of the medical instrument or expandable member. The blocking member may function to increase pressure and/or accuracy of a substance being delivered or expelled from the medical instrument or expandable member.

The blocking member may function to assist in moving tissue or objects away from a distal end of the tubular member, needle or both. The blocking member may function to assist in moving tissue or objects away from a distal end of the tubular member, needle or both by adding additional surface area to the expandable member that comes into contact with the tissue or objects when the expandable member is expanded into the expanded configuration.

The blocking member may be a sleeve or a collar. The blocking member may be a membrane or a fabric. The blocking member may be made of an elastic, resilient, expandable, flexible, stretchable, and/or complaint member. The blocking member may be substantially or entirely impermeable to fluid or the substance. The blocking member may be made of a plastic, rubber, or elastic material. The blocking member may be made of a EPDM, TPO, TPU material.

The blocking member may be provided or disposed along or about an entire length, perimeter, and/or circumference of the expandable member. Such a blocking member preferably has at least one aperture defined in the blocking member, described further below.

The blocking member may be disposed at or along only a portion of the length, perimeter, and/or circumference of the expandable member. For example, the blocking member may be located at only a distal end or portion of the expandable member, at only a proximal end or portion of the expandable member, or at only a center location or portion of the expandable member, or a combination thereof.

The blocking member may be disposed over or located on top of at least a portion of the fingers of the expandable member so that the fingers are not exposed to the site of interest of interest in the anatomy during a medical procedure. The blocking member may be disposed under or inside or within at least a portion of the expandable member so that the fingers are exposed to the site of interest in the anatomy during a medical procedure. The blocking member may be weaved under and over adjacent fingers so that some fingers are exposed inside the anatomy during a medical procedure, while other fingers are blocked or covered by the blocking member.

The blocking member may be directly connected to one or more of the fingers, to a distal end of the tubular member, to a distal end of the needle, to an inside portion of the needle, to a distal end of the expandable member, or a combination thereof. The blocking member may be individual strips that are provided in between and connected to adjacent fingers.

The blocking member may comprise one or more apertures. The one or more apertures in the blocking members may function to provide an area or opening through which the substance can be delivered, directed, deflected, distributed, and/or expelled through the blocking member. The one or more apertures defined in the blocking member may be circular, oval, slits, cuts, or a combination thereof. The size of all of the apertures in the blocking member may be the same. The size one or more of the apertures in the blocking member may be the different and/or randomly disposed. For example, the blocking member may comprise larger apertures at a proximal portion thereof compared to apertures at a central or distal portion thereof, or vice versa.

The one or more apertures may be arranged or located along an entire length of the blocking member. The one or more apertures may be arranged or located only along a selected portion thereof, such as only the proximal portion of the blocking member, only a distal portion of the blocking member, or only a central portion of the blocking member, or a combination thereof (e.g., only the distal and central portion of the blocking member, only the proximal and central portion of the blocking member).

The medical device, the medical instrument, or both, may be in fluid communication with one or more substance sources. A substance source may be a bag, container, reservoir, or any other storage medium configured to store one or more substances. The medical device, the medical instrument, the tubular member, or a combination, may be in fluid communication with the substance source via one or more tubes or delivery lines.

The substance may be one or more substances or agents used to clean and/or treat the anatomy and/or promote recovery from an injury or ailment. For example, the substance may be a medicine, anesthetic, drug, protein, hormone, medicine or mendicant, paste, fluid, therapy fluid, saline, alcohol, ethanol, or a combination thereof.

During a medical procedure, the substance may be moved or transported from the substance source to the medical device or the medical instrument, through the tubular member, and then delivered, directed, deflected, distributed, and/or expelled through or from a distal end of the tubular member though the expandable member.

The substance may be moved, transported, and/or expelled by manipulating one or more user controls located on the medical device, the medical instrument, at a remote location, or a combination thereof. For example, the substance may be moved or transported from the substance source to the medical device or instrument and then delivered, directed, deflected, distributed, and/or expelled from the expandable member by moving, depressing, or otherwise manipulating one or more buttons, levers, triggers, knobs, foot pedals, or a combination thereof. The medical device, the medical instrument, the substance source, or a combination thereof substance may be programmed or configured to be move, transport, deliver, direct, deflect, distribute, and/or expel the substance automatically after the expandable member is moved into the expanded configuration, or a predetermined time after the expandable member is moved into the expanded configuration. The medical device, the medical instrument, the substance source, or a combination thereof substance may be programmed or configured to automatically stop, cease, or discontinue movement, transport, delivery, distribution, and/or expelling the substance automatically after the expandable member is moved into the collapsed configuration.

Figure 1:
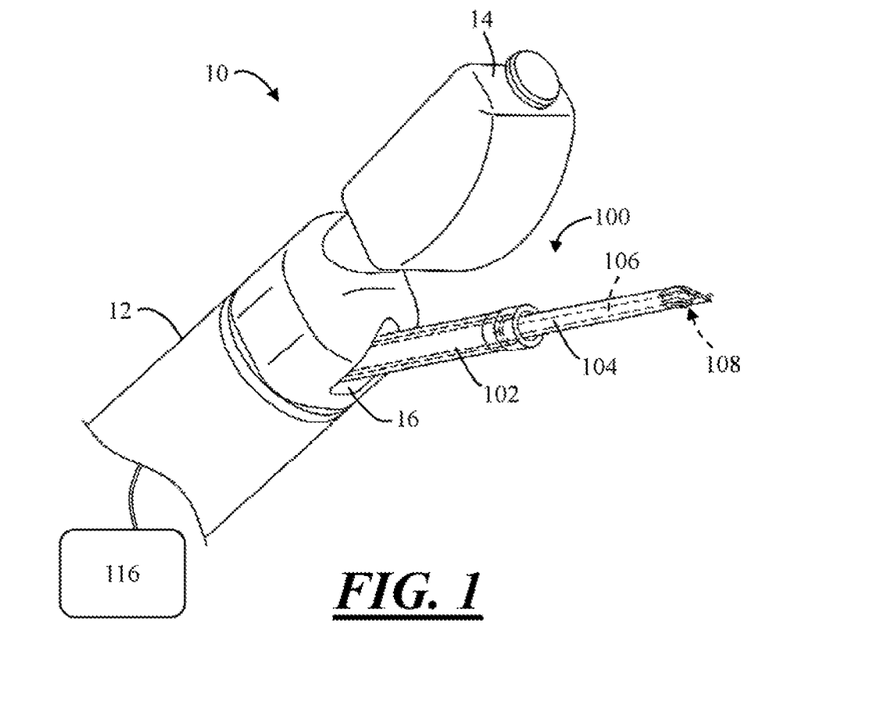
FIG. 1 is a perspective view of a medical device that includes a medical instrument according to these teachings.

FIG. 1 illustrates a medical device 10. The medical device 10 comprises a bronchoscope 12 and a viewing device 14, which may be an ultrasound and/or optical viewing device. The medical device 10 comprises an aperture 16 through which a medical instrument 100 extends.

The medical instrument 100 comprises a sheath 102, and a needle 104 located inside of the sheath 102. The medical instrument 100 comprises a tubular member 106 located inside of the needle 104, and an expandable member 108 located at a distal end of the tubular member 106. The tubular member 106 is in fluid communication with a substance source 116. The expandable member 108 is illustrated in a closed or collapsed configuration, where the expandable member 108 is located inside or distal of a distal end of the needle 104.

Figure 2:
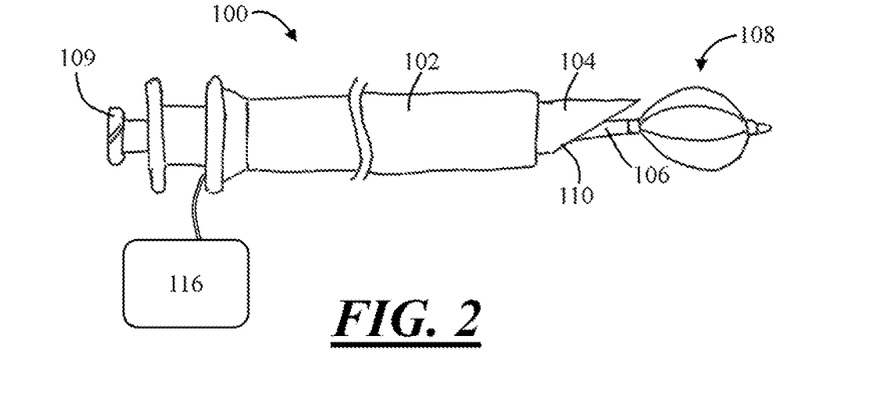
FIG. 2 is a side view of a medical instrument.

FIG. 2 illustrates a medical instrument 100 that can be used with or without the medical device 10 illustrated at FIG. 1. The medical device 100 comprises a sheath 102, a needle 104 located inside the sheath 102, and a tubular member 106 located inside the needle 104. The tubular member 106 is in fluid communication with the substance source 116. An expandable member 108 is connected to a distal end of the tubular member 106.

The tubular member 106 is moveable inside the needle 104. When the tubular member 106 is moved in a distal direction (to the right, in the orientation illustrated in FIG. 2), and the expandable member 108 is moved or extended beyond a distal end 110 of the needle 104, the expandable member 108 is configured to expand into the open or expanded configuration illustrated in FIG. 2. When the tubular member 106 is moved or retracted in a proximal direction (to the left, in the orientation illustrated in FIG. 2), and the expandable member 108 is moved or retracted into the needle 104 and within a distal end 110 of the needle 104, the expandable member 108 is configured to collapse into the closed or collapse configuration illustrated in FIG. 1.

The medical instrument 100 includes one or more user controls 109. The user control 109 can be manipulated to move or transport a substance from the substance source 116, through the tubular member 106, and then deliver, direct, deflect, distribute, and/or expel the substance from the expandable member 108. Similar user controls can be located on the medical device 10 of FIG. 1 to perform the same substance delivery functions. It is understood that the expandable member 108 of FIG. 2 can be replaced with any of the expandable members 108 illustrated in the following Figures and/or described throughout this disclosure.

Figure 3:
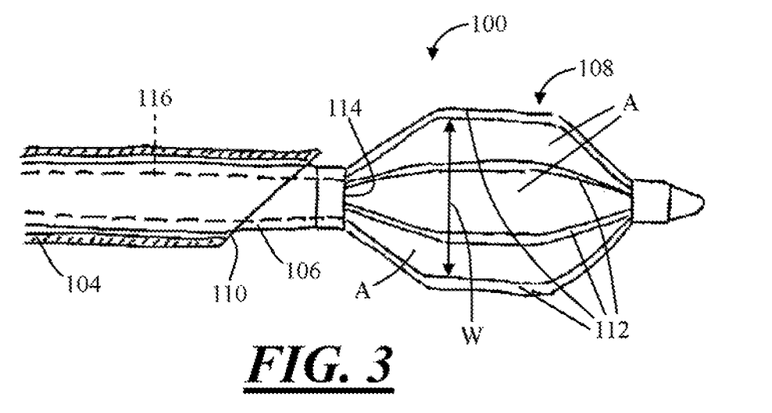
FIG. 3 is a partial side view of the medial instrument.

FIG. 3 illustrates the expandable member 108 in an open or expanded configuration. The expandable member 108 comprises a plurality of fingers 112 that are connected to, or extend from, a distal end 114 of the tubular member 106. The fingers 112 are configured to expand after the expandable member 108 is at least partially moved past or distally beyond the distal end 110 of the needle 104. A gap or aperture A is defined between adjacent fingers 112.

In the open or expanded configuration, a cross-sectional size or width W of the expandable member 108 is greater than a corresponding cross-section size or diameter of the tubular member 106 and the needle 104.

Figure 4:
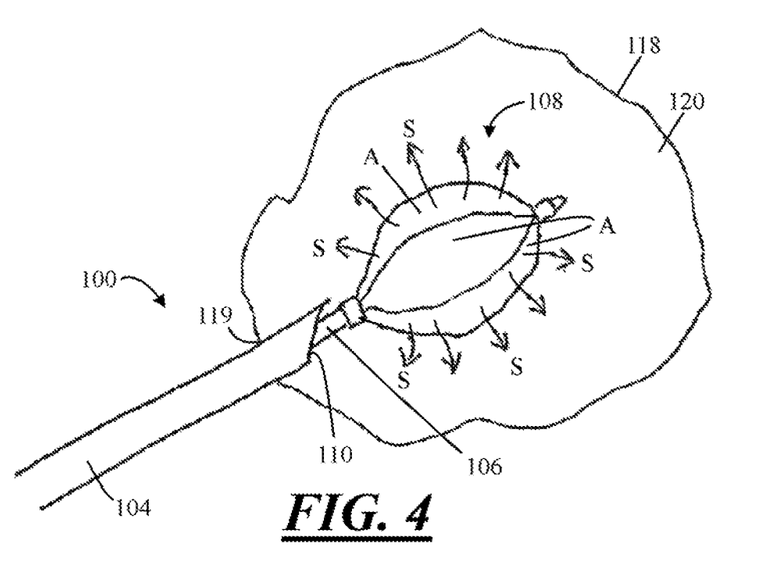
FIG. 4 is a side view of the medial instrument of FIG. 3 inside the anatomy.

FIG. 4 illustrates the medical instrument 100 of FIG. 3. During use, the distal end 110 of the needle 104 may be used to pierce the anatomy 118 at a puncture point 119 so that the needle 104 can be inserted into the anatomy 118 and then directed or steered towards a site of interest 120 in the anatomy 118.

The tubular member 106 can then be moved or extended in a distal direction so that the expandable member 108 is moved past or distally beyond the distal end 110 of the needle 104 so that the expandable member 108 can expand into the expanded configuration. Expanding the expandable member 108 may function to move or push tissue away from the distal end 110 of the needle 104 and/or the distal end 114 of the tubular member 106 to reduce or eliminate any tissue or other obstruction or interference with the distal end 110 of the needle 104 and/or the distal end 114 of the tubular member 106.

A substance S can then be moved or transported from the substance source 116, through the tubular member 106, and then delivered, directed, deflected, distributed, and/or expelled from the distal end 114 of the tubular member 106 via the expandable member 108 through the gaps or apertures A between the fingers 112, as illustrated by the arrows. The substance S can be radially directed out from the expandable member 108 from an entire circumference or perimeter of the expandable member 108.

By expanding the expandable member 108 and moving or pushing the tissue away from the distal end 110 of the needle 104 and/or the distal end 114 of the tubular member 106, the substance S can be delivered, directed, deflected, distributed, and/or expelled from the expandable member 108 and onto the desired tissue without the tissue contacting, blocking, deflecting, and/or otherwise obstructing the substance S from being expelled.

Moreover, by not having tissue contact, block, deflect, or otherwise obstruct the substance S from being expelled, the substance S can be delivered or provided to the entire site of interest 120, without having to reposition, re-orient, and/or manipulate the location or position of the medical instrument 100 and/or expandable member 108 inside the anatomy 118, which may reduce time of the medical procedure and/or reduce trauma to the patient.

Furthermore, by not having the tissue contact, block, deflect or obstruct substance S delivery from the tubular member 106, chances of the substance S leaking back from the tubular member 106 towards the puncture point 119 and out of the anatomy 120 is reduced or eliminated.

Furthermore, by not having the tissue contact, block, deflect or obstruct the distal end 110 of the needle 104 and/or the distal end 14 of the tubular member 106, a technician can view the medical device 100 inside the anatomy 118.

Lastly, by not having the tissue contact, block, deflect or obstruct substance S delivery from the tubular member 106, unintentionally delivering or directing substance S to tissue not intended to be treated with the substance S is reduced or eliminated.

Figure 5:
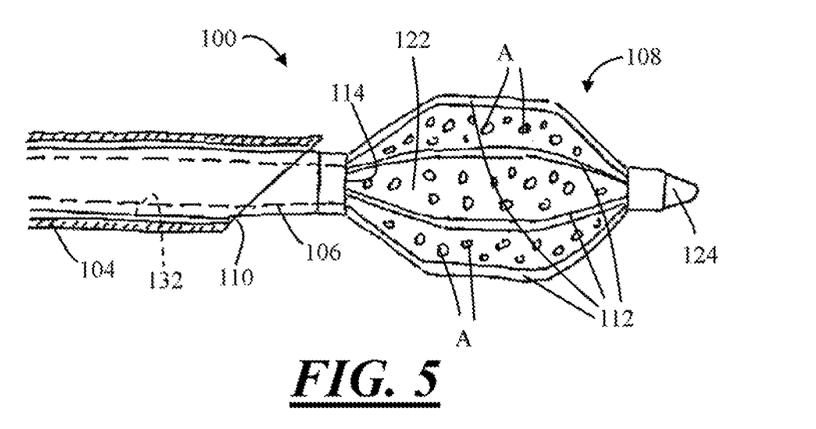
FIG. 5 is a partial side view of the medial instrument.

FIG. 5 illustrates the expandable member 108 of the medical instrument 100 in an expanded configuration. The features, functions, and benefits of the medical instrument 100 of FIG. 5 may be substantially similar to those described above at FIG. 2-4, so only the differences of FIG. 5 will be discussed below.

The medical instrument 100 comprises a blocking member 122. The blocking member 122 comprises a plurality of apertures A that extend through a thickness of the blocking member 122.

The blocking, member 122 may be a sleeve or collar that is disposed over, onto, and/or around a circumference or perimeter of the expandable member 108. The blocking member 122 may be a single member that extends or is stretched over the fingers 112, and is connected to both of the distal end 114 of the tubular member 106 and a distal portion 124 of the expandable member 108 or tubular member 106. In some configurations, instead of being connected of the distal end 114 of the tubular member 106, however, the blocking member 122 may be connected to the distal end 110 of the needle 104, or connected or attached to an inside portion 132 of the needle 104, like in FIG. 8.

In some configurations, the blocking member 122 may be connected to each of the fingers 112. In some configurations, the blocking member 122 may be provided as individual or discrete pieces or strips that are arranged between and connected to adjacent fingers 112. In such a configuration, the blocking member 122 may, or may not, be connected to the distal end 114 of the tubular member 106 and/or the distal portion 124 of the expandable member 108 or tubular member 106.

Figure 6:
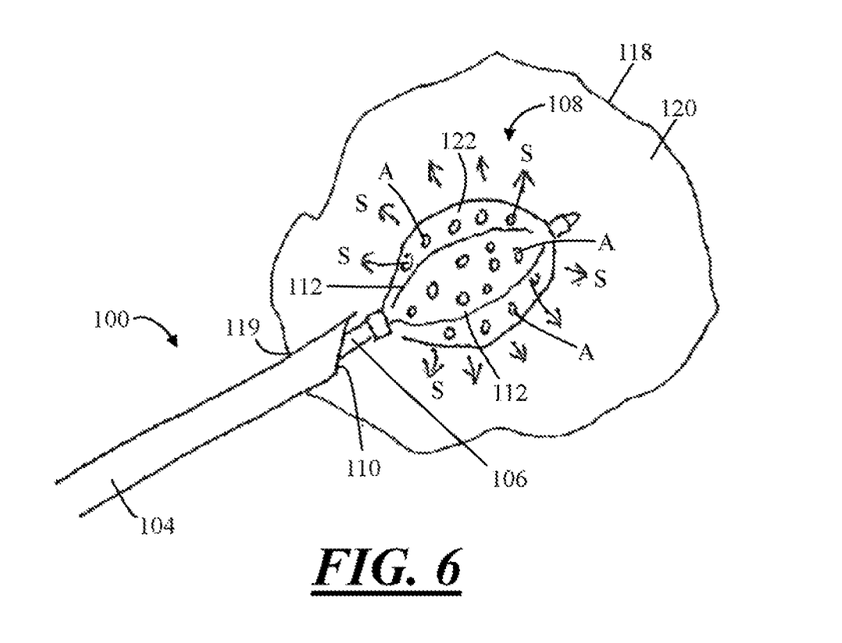
FIG. 6 is a side view of the medial instrument of FIG. 5 inside the anatomy.

FIG. 6 illustrates the medical instrument 100 of FIG. 5. During use, similar to the description above at FIG. 4, the distal end 110 of the needle 104 may be used to pierce the anatomy 118 at a puncture point 119, and then the needle 104 can be directed and steered towards a site of interest 120 inside the anatomy 118.

The tubular member 106 can then be distally extended from inside the needle 104 so that the expandable member 108 is expanded. Expanding the expandable member 108 may function to move or push tissue at the site of interest 120 away from the distal end 110 of the needle 104 and/or the distal end 114 of the tubular member 106.

A substance S can then be moved or transported from the substance source 116, through the tubular member 106, and then delivered, directed, deflected, distributed, and/or expelled through or from the apertures A defined in the blocking member 122, as illustrated by the arrows. The substance S can be radially delivered, directed, distributed, and/or expelled from the expandable member 108 from an entire circumference or perimeter of the expandable member 108.

The blocking member 122 may function to assist in moving or pushing tissue or objects at the site of interest 120 away from the distal end 110 of the needle 104 and/or the distal end 114 of the tubular member 106. That is, while tissue can be moved or pushed away with only the fingers 112 of the expandable member 108 like in FIGS. 3 and 4, the blocking member 122 functions to add additional surface area to the expandable member 108 for moving or pushing tissue or objects that may otherwise fall into or between the fingers 112 and may not be moved or pushed with the expandable member 108 of FIGS. 3 and 4, for example.

Additionally, or alternatively, by expelling the substance S through only the apertures A defined in the blocking member 122, as opposed to from between the large gaps or apertures A defined between fingers 112 in FIGS. 3 and 4, for example, the substance S may be expelled with greater pressure and accuracy compared to when the substance S is expelled from the configuration illustrated in FIGS. 3 and 4. That is, in FIGS. 3 and 4, different amounts of substance S may be expelled or delivered from a proximal portion of the expandable member 108 compared to a distal portion of the expandable member 108.

The blocking member 122 also functions to block delivery of the substance S to areas in the anatomy that are not aligned with the apertures A, while delivering, directing, deflecting, distributing, and/or expelling the substance S where the apertures A are located.

Figure 7:
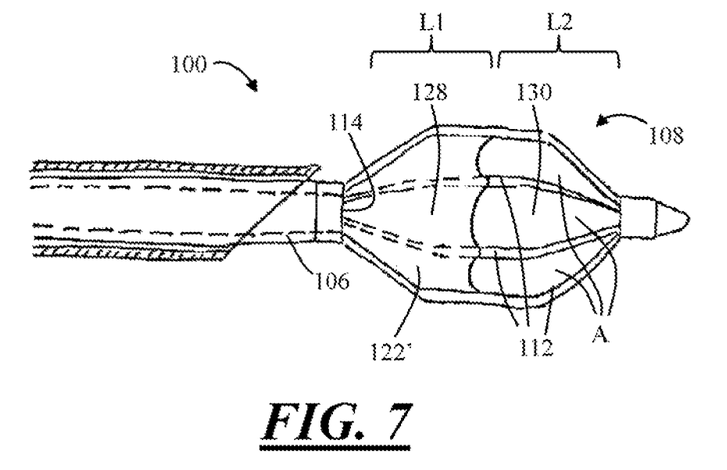
FIG. 7 is a partial side view of the medial instrument.

FIG. 7 illustrates the expandable member 108 of the medical instrument 100 in an expanded configuration. The features, functions, and benefits of the medical instrument 100 of FIG. 7 may be substantially similar to those described above at FIG. 1-6, so only the differences of FIG. 7 will be discussed.

The medical instrument 100 comprises a blocking member 122'. The blocking member 122' may be a sleeve or collar that is disposed around a circumference or perimeter of the expandable member 108, but only at a proximal portion 128 of the expandable member 108. A proximal end of the blocking member 122' may be connected or attached to the distal end 114 of the tubular member 106.

The blocking member 122' may be substantially free of any apertures. A distal portion 130 of the expandable member 108 may be free of any blocking members.

The blocking member 122' may have a length L1 that is substantially the same as the length L2 of the distal portion 130 of the expandable member 108 that is not covered by any blocking member. Of course, in some configurations, length L1 may be greater than or less than the length L2.

During a medical procedure, the substance S is delivered, directed, distributed, and/or expelled from between the gaps or apertures A defined between the fingers 112 at the distal end 130 of the expandable member 108. The blocking member 122' functions to block delivery of the substance S to areas in the anatomy that are located at or near the blocking member 122', at the proximal portion 128 of the expandable member 108.

Advantageously, the blocking member 122' provides a technician with the ability to sufficiently move tissue or objects away from the distal end 110 of the needle 104 and/or tubular member 106 with the expandable member 122, while reducing or minimizing the areas from where the substance S can be expelled from the expandable member 122. This provides a technician with the ability to control exactly where the substance S is expelled or delivered from so that only tissue desired to be treated with the substance S is treated.

Moreover, by delivering or expelling the substance S only from a center and/or distal portion of the expandable member 108, chances of the substance S leaking back towards the distal end 114 of the tubular member 106 and/or needle 104 is reduced or prevented. This reduces chances of the substance S flowing into or inside the needle 104 and/or tubular member 106 or even out of the anatomy 120 through a puncture point 119 where the needle 101 penetrates the anatomy 120.

Figure 8:
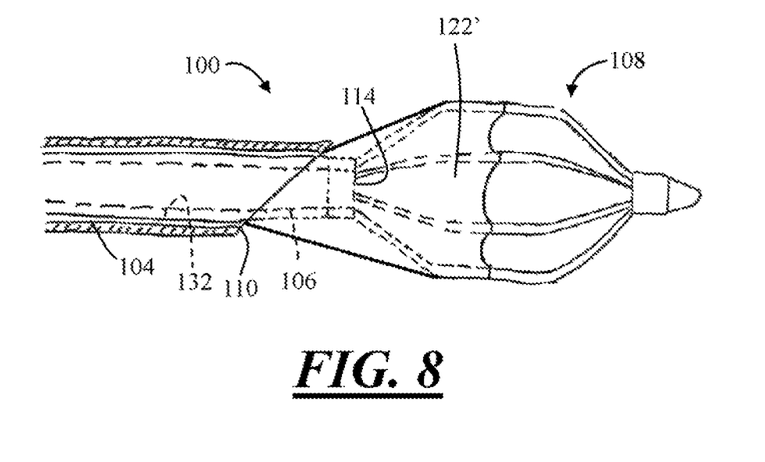
FIG. 8 is a partial side view of the medial instrument.

The medical instrument 100 of FIG. 8 is substantially similar to the medical instrument 100 illustrated at FIG. 7, except that instead of the proximal end of the blocking member 122' being connected or attached to the distal end 114 of the tubular member 106 like in FIG. 7, the proximal end of the blocking member 122' is connected or attached to the distal end 110 of the needle 104, or to an inner wall 132 of the needle 104. By attaching the blocking member 122' to the distal end 110 of the needle 104, or to an inner wall 132 of the needle 104, chances of the substance S flowing or dripping back into the interior portion 132 of the needle 104 is reduced or eliminated.

Figure 9:
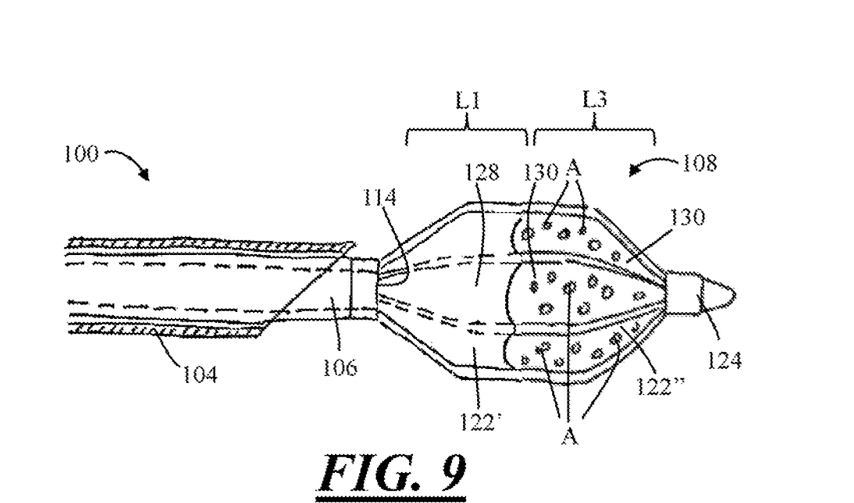
FIG. 9 is a partial side view of the medial instrument.

The medical instrument 100 of FIG. 9 comprises a blocking member 122' at a proximal portion 128 of the expandable member 108, and another blocking member 122" at a distal end 130 of the expandable member 108. Blocking member 122" may comprise a plurality of apertures A defined in a thickness thereof, while blocking member 122' may be substantially free of any apertures.

The blocking member 122' that covers the proximal portion 128 of the expandable member 108 may have a length L1 that is substantially the same as the length L3 of the blocking member 122" that covers the distal end 130 of the expandable member 108. Of course, in some configurations, length L1 may be greater than or less than length L3.

Figure 10:
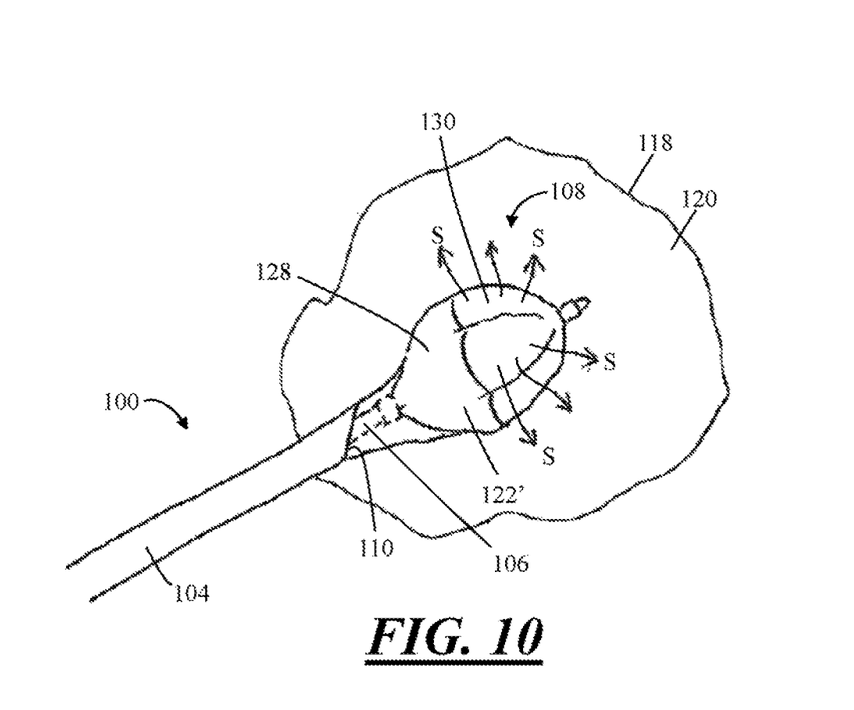
FIG. 10 is a side view of the medial instrument of FIGS. 7, 8, and/or 9 inside the anatomy.

FIG. 10 illustrates the medical instrument 100 of FIGS. 7, 8, and/or 9. After the distal end 110 of the needle 104 pierces the anatomy 118 and the needle 104 is directed or steered towards a site of interest 120 in the anatomy 118, the tubular member 106 can be extended from the needle 104 so that the expandable member 108 is expanded.

Expanding of the expandable member 108 may function to move or push tissue away front the distal end 110 of the needle 104 and/or the distal end 114 of the tubular member 106.

A substance S can then be transported from the substance source 116 (FIG. 1), through the tubular member 106, and then delivered, directed, distributed, and/or expelled through the distal end 130 of the expandable member 108.

More specifically, for FIGS. 7 and 8, the substance S is delivered, directed, deflected, distributed, and/or expelled through the apertures A defined between the fingers 112 at the distal end 130 of the expandable member. Because the blocking member 122' is free of any apertures, the blocking member 122' functions to block delivery of the substance S to areas in the anatomy that are located at or near the blocking member 122', at the proximal portion 128 of the expandable member 108.

For FIG. 9, the substance S is delivered, directed, deflected, distributed, and/or expelled through the apertures A defined in the blocking member 122" at the distal portion 130 of the expandable member 108. Because the blocking member 122' is free of any apertures, no substance S is delivered, directed, distributed, and/or expelled through the blocking member 122' or the proximal portion 128 of the expandable member 108.

LISTING OF REFERENCE NUMERALS 10 medical device
12 bronchoscope
14 viewing device
16 aperture
100 medical instrument
102 sheath
104 needle
106 tubular member
108 expandable member
109 user control
110 distal end of needle 104
112 fingers
114 distal end of tubular member 106
116 substance source
118 anatomy
119 puncture point
120 site of interest of anatomy 118
122 blocking member
122' proximal portion blocking member
122" distal portion blocking member
124 distal portion of the expandable member 108 or tubular member 106
128 proximal portion of the expandable member 108
130 distal portion of the expandable member 108
132 inside portion of the needle 104
A apertures
W cross-sectional size or width of the expandable member 108
S substance Features or elements included in any one of the figures of this disclosure can be added or combined with other features or elements in other figures of this disclosure. Moreover, features, elements, and/or the function of features and elements described in any part of this disclosure can be added to or apply any of the figures, even though they are not expressly shown or described in those figures.

The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

The invention claimed is:

1. A medical instrument comprising:
    a substance delivery apparatus including:
        a needle;
        an expandable member enabled to extend distally beyond a distal end of the needle, the expandable member supporting a plurality of fingers that extend from a proximal end of the expandable member to a distal end of the expandable member, the plurality of fingers being further configured to expand in response to the expandable member being moved in a distal direction beyond the distal end of the needle and configured to collapse in response to the expandable member being moved in a proximal direction into the needle;
        a tubular member in fluid communication with a substance source and having a distal end fluidly coupled to the proximal end of the expandable member and configured to deliver a substance from the substance source through the proximal end of the expandable member;
        a first blocking member that covers a portion of the expandable member and that defines at least one opening configured to deliver the substance, the blocking member being configured to permit the substance passing through the proximal end of the expandable member to be delivered through the opening and to flow without interference out of the substance delivery apparatus in the distal direction and to prevent the substance from flowing past the expandable member in the proximal direction; and
        a second blocking member that is located distal of the blocking member, wherein the second blocking member comprises a plurality of apertures configured to allow the substance to pass therethrough.

2. The medical instrument according to claim 1, wherein the blocking member is substantially free of any apertures.

3. The medical instrument according to claim 1, wherein a length of the blocking member is substantially the same as a length of the second blocking member.

* * * * *